US009011407B2

(12) United States Patent
Harig

(10) Patent No.: US 9,011,407 B2
(45) Date of Patent: Apr. 21, 2015

(54) PRE-EVACUATABLE OR PRE-EVACUATED CONTAINER FOR MEDICAL PURPOSES

(75) Inventor: Volker Harig, Saarbrücken (DE)

(73) Assignee: PFM Medical AG, Cologne (DE)

( * ) Notice: Subject to any disclaimer, the term of this patent is extended or adjusted under 35 U.S.C. 154(b) by 359 days.

(21) Appl. No.: 12/167,954

(22) Filed: Jul. 3, 2008

(65) Prior Publication Data

US 2009/0012493 A1 Jan. 8, 2009

(30) Foreign Application Priority Data

Jul. 4, 2007 (DE) ............... 20 2007 009 414 U

(51) Int. Cl.
| | |
|---|---|
| *A61J 1/18* | (2006.01) |
| *A61J 1/14* | (2006.01) |
| *A61M 1/00* | (2006.01) |
| *B65D 88/50* | (2006.01) |
| *B65D 88/42* | (2006.01) |

(52) U.S. Cl.
CPC .... *A61M 1/0003* (2013.01); *B65D 2543/00435* (2013.01); *A61M 1/0001* (2013.01); *A61M 1/0058* (2013.01); *B65D 2543/00518* (2013.01); *B65D 88/50* (2013.01); *B65D 88/42* (2013.01); *B65D 2543/00972* (2013.01); *B65D 2543/00527* (2013.01); *A61M 1/0023* (2013.01); *B65D 2543/00555* (2013.01); *B65D 2543/00537* (2013.01)

(58) Field of Classification Search
CPC ............ A61M 1/0001; A61M 1/0023; A61M 1/0058; A61M 2001/0001; A61M 2001/0023; A61M 2001/0058; B65D 43/0204; B65D 43/0206; B65D 43/0237; B65D 43/0239; B65D 43/06; B65D 88/42; B65D 88/50; B65D 2543/00435; B65D 2543/00518; B65D 2543/00555; B65D 2543/00972; B65D 2543/00527; B65D 2543/00537
USPC ......... 604/318, 319, 322, 540, 404, 541, 542, 604/543, 544, 321; 220/200–305, 309.1, 220/309.2, 310.1, 795, 849, 345.6, 803, 220/804, 806, 378, 614, 681
See application file for complete search history.

(56) References Cited

U.S. PATENT DOCUMENTS 3,289,879 A * 12/1966 Williams ................ 220/378
3,381,687 A   5/1968 Andersen et al.
(Continued)

FOREIGN PATENT DOCUMENTS

| CA | 2310637 | 11/1998 |
|---|---|---|
| DE | 1491630 | 7/1969 |

(Continued)

OTHER PUBLICATIONS

European Search Report for corresponding EP application No. 08011572.8-1257/2011528, Apr. 9, 2009.

*Primary Examiner* — Adam Marcetich
(74) *Attorney, Agent, or Firm* — Grossman, Tucker, Perreault & Pfleger, PLLC

(57) ABSTRACT

A pre-evacuatable or pre-evacuated container for medical purposes is provided. The container comprises a container body which is open at one side with a peripherally extending container wall and a bottom, and a cover element. The peripherally extending container wall of the container body has an end groove, into which a sealing element for sealing off the container body with respect to the cover element is or can be inserted.

22 Claims, 4 Drawing Sheets

(56) References Cited

U.S. PATENT DOCUMENTS

| | | | |
|---|---|---|---|
| 3,942,679 A * | 3/1976 | Starr | 220/784 |
| 3,945,392 A | 3/1976 | Deaton et al. | |
| 4,015,745 A * | 4/1977 | Petrangelo | 220/320 |
| 4,027,777 A * | 6/1977 | Blanke, Jr. | 220/295 |
| 4,086,925 A | 5/1978 | Dodge | |
| 4,184,510 A * | 1/1980 | Murry et al. | 137/565.23 |
| 4,195,633 A | 4/1980 | Nehring et al. | |
| 4,298,204 A * | 11/1981 | Jinkins | 277/641 |
| 4,379,455 A | 4/1983 | Deaton | |
| 4,444,332 A * | 4/1984 | Widen et al. | 220/792 |
| 4,564,359 A | 1/1986 | Ruhland | |
| 4,642,093 A * | 2/1987 | Harle | 604/543 |
| 4,675,010 A * | 6/1987 | Siposs et al. | 604/319 |
| 4,782,976 A * | 11/1988 | Kenyon, 2nd. | 220/781 |
| 4,890,757 A * | 1/1990 | Robbins, III | 220/675 |
| 4,989,745 A | 2/1991 | Schneider | |
| 4,995,513 A * | 2/1991 | Rosler | 206/446 |
| 5,025,948 A * | 6/1991 | Fixon | 220/360 |
| 5,143,219 A * | 9/1992 | Yates, Jr. | 206/508 |
| 5,163,576 A * | 11/1992 | Galer | 220/792 |
| 5,381,918 A * | 1/1995 | Dahl | 220/784 |
| 5,395,003 A * | 3/1995 | Matsuda | 220/270 |
| 5,427,266 A * | 6/1995 | Yun | 220/377 |
| 5,538,154 A * | 7/1996 | Von Holdt | 220/277 |
| 5,540,349 A * | 7/1996 | Philips | 220/780 |
| 5,645,540 A * | 7/1997 | Henniges et al. | 604/320 |
| 5,730,309 A * | 3/1998 | Jiradejnunt et al. | 220/276 |
| 5,944,214 A * | 8/1999 | Conti et al. | 220/304 |
| 5,944,703 A * | 8/1999 | Dixon et al. | 604/319 |
| 5,960,837 A * | 10/1999 | Cude | 141/65 |
| 6,098,833 A * | 8/2000 | von Holdt et al. | 220/659 |
| 6,135,286 A * | 10/2000 | Strumor | 206/573 |
| 6,152,902 A * | 11/2000 | Christian et al. | 604/320 |
| 6,170,691 B1 * | 1/2001 | Morris et al. | 220/304 |
| 6,183,452 B1 | 2/2001 | Bodmer et al. | |
| 6,183,453 B1 | 2/2001 | Swisher | |
| 6,332,555 B1 * | 12/2001 | Stangier | 220/562 |
| 6,405,887 B1 * | 6/2002 | Cargile | 215/379 |
| 6,604,647 B1 * | 8/2003 | Luburic | 220/270 |
| 6,635,028 B1 * | 10/2003 | Ielpo et al. | 604/27 |
| 7,153,294 B1 | 12/2006 | Farrow | |
| 2002/0162846 A1 * | 11/2002 | Mercier | 220/780 |
| 2002/0175172 A1 * | 11/2002 | Diesterbeck | 220/782 |
| 2004/0102761 A1 * | 5/2004 | Ahmed | 604/540 |
| 2004/0112906 A1 * | 6/2004 | von Holdt, Jr. | 220/657 |
| 2004/0116902 A1 | 6/2004 | Grossman et al. | |
| 2006/0138156 A1 * | 6/2006 | Kellerer et al. | 220/782 |
| 2007/0158348 A1 * | 7/2007 | Kosmyna et al. | 220/23.87 |
| 2009/0236354 A1 * | 9/2009 | Alvares et al. | 220/783 |

FOREIGN PATENT DOCUMENTS

| | | |
|---|---|---|
| DE | 8420384 | 9/1984 |
| DE | 8530626 | 4/1986 |
| DE | 8604614 | 6/1986 |
| EP | 0 378 866 | 1/1989 |
| EP | 1 157 933 A2 | 5/2001 |
| GB | 2 240 332 | 7/1991 |
| WO | WO 83/01767 | 5/1983 |

* cited by examiner

PRE-EVACUATABLE OR PRE-EVACUATED CONTAINER FOR MEDICAL PURPOSES

CROSS-REFERENCE TO RELATED APPLICATIONS

This application claims priority to German Patent Application No. 20 2007 009 414.0, entitled "Pre-evacuatable or pre-evacuated container for medical purposes", filed Jul. 4, 2007, the entirety of which is hereby incorporated by reference.

BACKGROUND OF THE INVENTION

1. Field of the Invention

Embodiments of the present disclosure concern a pre-evacuatable or pre-evacuated container for medical purposes.

2. Description of the Related Art

Pre-evacuated containers for medical purposes in the form of Redon flasks are known in the state of the art. Redon flasks of that kind have, in particular, a maximum reduced pressure of 98,000 Pascals. They are in the form of a one-part bulbous body of plastic material, with connection portions being fitted on the top side of the container. A pressure indicator and a hose are attached thereto. Such a kind of Redon vacuum flask is described, for example, in DE 84 20 384 U1 or US No. 2004/0116902 or DE 86 04 614 U1.

U.S. Pat. No. 4,989,745 also describes a container which is evacuatable by way of a pump, for non-medical purposes. The container disclosed therein is intended for accommodating foodstuffs, chemicals, inks or dyes or the like and has a cylindrical body and a cover which are connected together by way of a deformable indicator element which is provided for sealing off the container body and the cover relative to each other. The deformable indicator element is disposed in line with the wall of the container body in parallel relationship with the cover or even in one piece therewith. The deformable indicator element is visible from the exterior and is thereby intended to be a display in respect of the evacuation condition of the container. If it is not visible from the exterior such a high reduced pressure obtains in the container that the cover is moved downwardly in the direction of the container body to such a degree that the indicator element is no longer visible from the exterior.

DE 14 91 630 A1 discloses a suction device for medical purposes, more specifically, for draining fluid from the thoracic cavity of a patient, where the suction device has a glass flask with a cover screwed thereon and to provide sealing integrity a seal over a sterile water as a water seal.

A disposal container for medical treatments is also described in DE 85 30 626 U1. It serves for receiving fluid body excretions introduced into drainage vessels, such as wound secretions, urine, and the like. The disposal container comprises a shaped portion of a plastic material of a capacity of up to 10 liters. The flask has a narrowed neck which is provided with a male screw thread and on to which is fitted a closure cap provided with suitable hoses in order to close the mouth opening of the flask in pressure medium-tight relationship.

In addition, U.S. Pat. No. 4,195,633 discloses a column of pleura drainage containers which can be evacuated by an external vacuum pump system. The respective containers are in the form of cylindrical containers with a cover which is screwed thereon and into which project connection portions for hoses. The containers comprise a plastic material or glass.

Still other drainage devices for thorax and pleura drainage procedures are known in the state of the art such as, for example, U.S. Pat. No. 4,086,925. In the case of those devices, respective screw covers are screwed on to the container, where connections for connecting hoses project into the screw-on cover.

The state of the art also discloses other pre-evacuated containers as are described for example in U.S. Pat. No. 6,183,452 B1 or CA 2,310,637. Containers of that kind serve to receive and also deliver blood from or to a patient and can also be used for autotransfusion of blood to a patient. With this system also hoses or connection portions for hoses project into a cover of a corresponding flask.

SUMMARY OF THE INVENTION

Embodiments of the present disclosure provide a pre-evacuatable or pre-evacuated container for medical purposes, in particular for use as Redon containers, which is as advantageous as possible in terms of manufacture and reliable in operation. Such containers, in particular, can be subjected without problem, to a reduced pressure of up to or over 90,000 Pascals.

That object may be attained by a pre-evacuatable or pre-evacuated container comprising a container body which is open at one side with a peripherally extending container wall, a bottom, and a cover element. The peripherally extending container wall of the container body may possess an end groove, into which a sealing element for sealing off the container body with respect to the cover element is or can be inserted.

Beneficially, this container configuration may provide a pre-evacuatable or pre-evacuated container for medical purposes, which, by virtue of the provision of an end groove with sealing element inserted therein in the peripherally extending container wall of the container body, is particularly well and reliably suitable for sealing off the container body with respect to the cover element. With this sealing arrangement, it is possible to provide a desired reduced pressure of up to or over 90,000 Pascals. By virtue of the provision of the end groove with the inserted sealing element, it is further possible to achieve improved sealing action than in the case of the containers which generally involve screw closures. In the case of such containers, the sealing elements can be displaced or can be tilted when the cover is being screwed on so that an optimum sealing effect is no longer possible. In contrast, with embodiments of the present disclosure, when the sealing element is inserted into the end groove, the sealing element is at the desired location and there is no risk of the sealing element being unintentionally displaced when the cover element is fit into position.

Advantageously, the sealing element may be provided in the form of an O-ring seal. Such an O-ring can be particularly well fitted into a peripherally extending end groove in the container wall of the container body. When the cover element is fitted in place, the O-ring seal can be compressed somewhat and thus is positioned in the end groove in the container wall in order to be able to achieve complete sealing integrity.

It has proven to be further advantageous, in certain embodiments, that the end portion the container wall comprise a reinforced configuration to receive the groove and, for example, is of a greater wall thickness than in the remaining region of the container body. This arrangement provides that there is a particularly high level of stability in the region which is available for sealing off the container body with respect to the cover element, in order to be able to carry the forces which occur between the cover element and the container body upon evacuation. Furthermore, this configuration provides that the groove can be so large that it is possible for the sealing element which is fitted into the groove to be of the optimum dimensions. That is to say, there is sufficient space for insertion of that sealing element.

In certain embodiments, the sealing element is releasably connected to the container body. For that purpose, a clamping or snap connection can be provided for connecting the cover element and the container body. The provision of such a clamping or snap connection permits the container to be closed and possibly opened again without any trouble, for example, in order to empty and clean the container. A clamping or snap connection is also found to be particularly advantageous when the cover element and the container body are joined for the first time, as such a connection permits a quicker connection to be made than, for example, a screw connection. Notably, a clamping or snap connection can be closed by simply fitting the cover element on to the container body and applying a pressure to the cover element but a screw connection requires the cover to be screwed completely on to the container, for if the cover is not screwed completely on the container a leak can occur. A clamping or snap connection is also found to be more reliable in comparison with a screw connection and thus affords better sealing integrity without further measures. Evacuation of the container can be effected directly after the cover element has been attached.

Furthermore, a rotary connection for releasably connecting the cover element and the container body is also possible, for example, in the manner of a Luer lock closure or a bayonet fixing. In this case also sealed closure of the container by means of a small number of movements is reliably possible.

In principle, it is alternatively also possible for the cover element and the container body to be fixedly connected together, in particular, welded together. By way of example, a cover element which is fitted in place on the container and which is held fast to the container body, for example, by a clamping or snap connection, can be connected thereto by welding in order to change the initially releasable connection between the cover element and the container body into a non-releasable connection therebetween. Such a non-releasable connection can be provided, for example, if there is no need for further emptying or cleaning of the container. and may also enable an even better sealing effect to be produced than that which is already provided by the sealing element in the end groove in the container wall. Such a non-releasable connection may also be provided, if the content of the container is not to be removed therefrom again as, for example, it is contaminated. It is then possible to reliably prevent the container from being opened by the welded connection.

Advantageously the container and/or the cover element may comprise polyvinyl chloride (PVC), polypropylene (PP), or polyethylene terephthalate (PETP). It is also possible to use a different plastic material for making the container and/or the cover element. The specified materials however make it possible to produce inexpensive containers which at the same time are stable.

Advantageously, embodiments of the container body may further comprise at least one reinforcing rib. In certain embodiments, there are provided, respectively, mutually oppositely disposed reinforcing ribs, for example, four reinforcing ribs. The at least one reinforcing rib extends along the container wall. It can further be provided that the at least one reinforcing rib extends along the container wall and the bottom of the container body. Reinforcing ribs of this kind enable the container body to remain stable, in respect of shape, upon evacuation. For at least this reason it has proven to be advantageous to provide mutually oppositely disposed reinforcing ribs so as to inhibit one-sided buckling distortion of the container body. It will be appreciated that, instead of four reinforcing ribs, in alternative embodiments, it is also possible to provide more than four reinforcing ribs and, optionally, also an odd number of reinforcing ribs which are distributed uniformly over the periphery of the container body. Depending on the respective configuration of the bottom of the container body, it can either be provided with, or can be without, a reinforcing rib or ribs. In such case, for example, four reinforcing ribs which extend along the container wall can come together in crossed-over relationship in the bottom of the container body. This configuration still further enhances the stability of the container body in terms of buckling distortion upon evacuation.

In addition, the container body can be provided with a scale means. The scale means serves to be able to ascertain the amount of content which has been sucked away within the container.

The cover element may be advantageously provided with at least one connection portion for the connection of a hose. There can further be provided a pressure indicator device in the cover element, for example, a pressure bellows which is known in the state of the art. Furthermore, the cover element can be provided with at least one suspension device for suspending the container from a holding device, in particular an infusion stand. If there is no need for the container to be hung up, it will be appreciated that such a suspension device can also be omitted.

Advantageously, the cover element may comprise a receiving space for receiving and/or embracing the portion, having the sealing element, of the container wall of the container body. In that case, the cover element can comprise a substantially flat portion, a rim portion which adjoins the portion and which is angled substantially at a right angle relative thereto, and a wall portion which is so arranged at a spacing relative to the rim portion that the receiving space remains between the rim portion and the wall portion to receive the portion of the container wall that has the sealing element. Thus, not only does the rim portion engage behind the end portion of the container wall, but that portion of the container wall is additionally also received by the wall portion which, together with the rim portion, forms the receiving space for receiving the end portion of the container wall. The sealing action can thus be still further optimized, as the end portion of the container wall is embraced as far as possible by the cover element and the configuration thereof.

The wall portion can also be of such a configuration so as to narrow in a direction away from the flat portion. By virtue of that arrangement, it is possible, on the one hand, to provide a stable connection in the region of the connection to the flat portion of the cover element so that the end portion of the container wall can be received in the receiving space in a stable fashion. On the other hand, by virtue of the narrowed configuration, a certain spring action is possible in the region of the wall portion that is remote from the flat portion of the cover element, so that the wall portion can bear even better against the end portion of the container wall.

Advantageously, the outside the rim portion may further comprise at least one gripping element for engaging the rim portion. Instead of just one gripping element, it is also possible to provide a plurality of gripping elements, where removal of the cover element from the container body can be still further facilitated. Since, in general terms, it is the sealing action between the cover element and the container body that is found to be very important, as removal of the cover element from the container body will only be required for emptying and cleaning the container, the provision of just one gripping element may be sufficient in certain embodiments for removing the cover element from the container body.

BRIEF DESCRIPTION OF THE DRAWINGS

In order further to describe the invention embodiments thereof are set forth in greater detail hereinafter with reference to the drawings in which.

DETAILED DESCRIPTION OF THE PREFERRED EMBODIMENT

Figure 1:
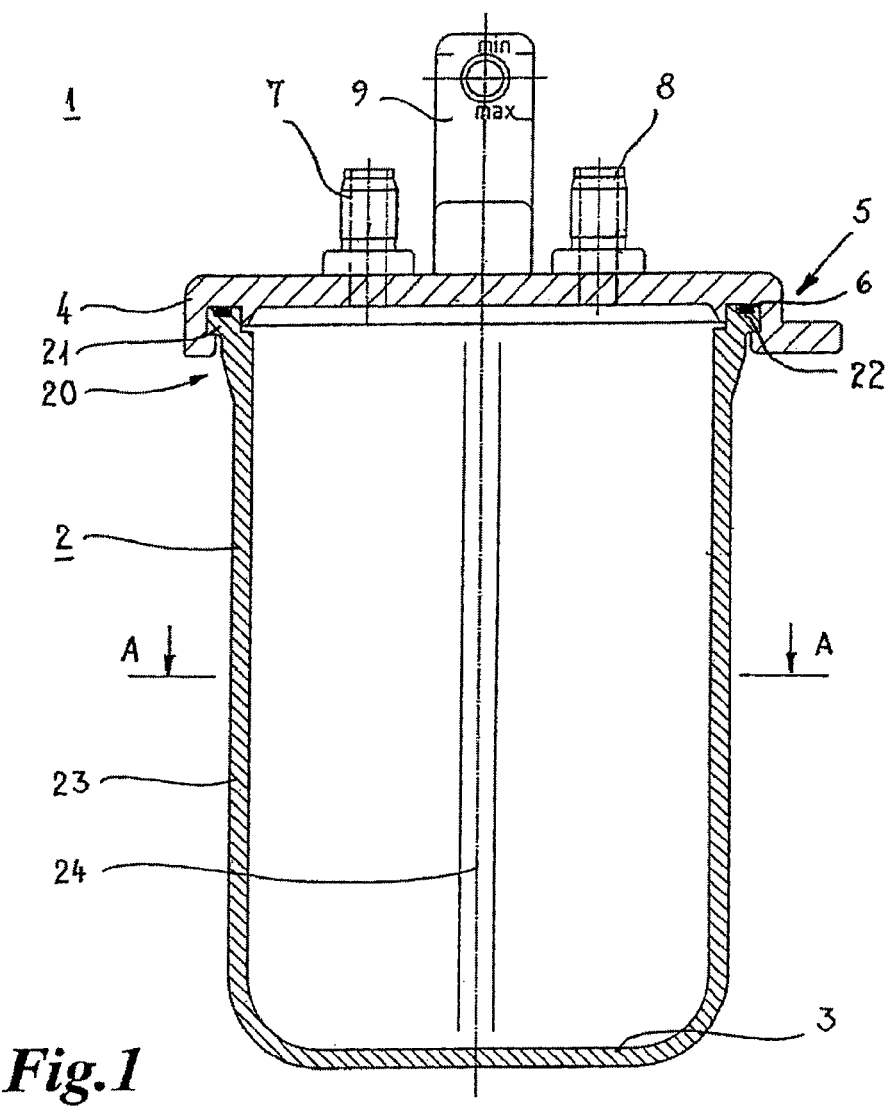
FIG. 1 shows a lateral view in section of an embodiment of a pre-evacuatable or pre-evacuated container according to the present disclosure for medical purposes.
Figure 4:
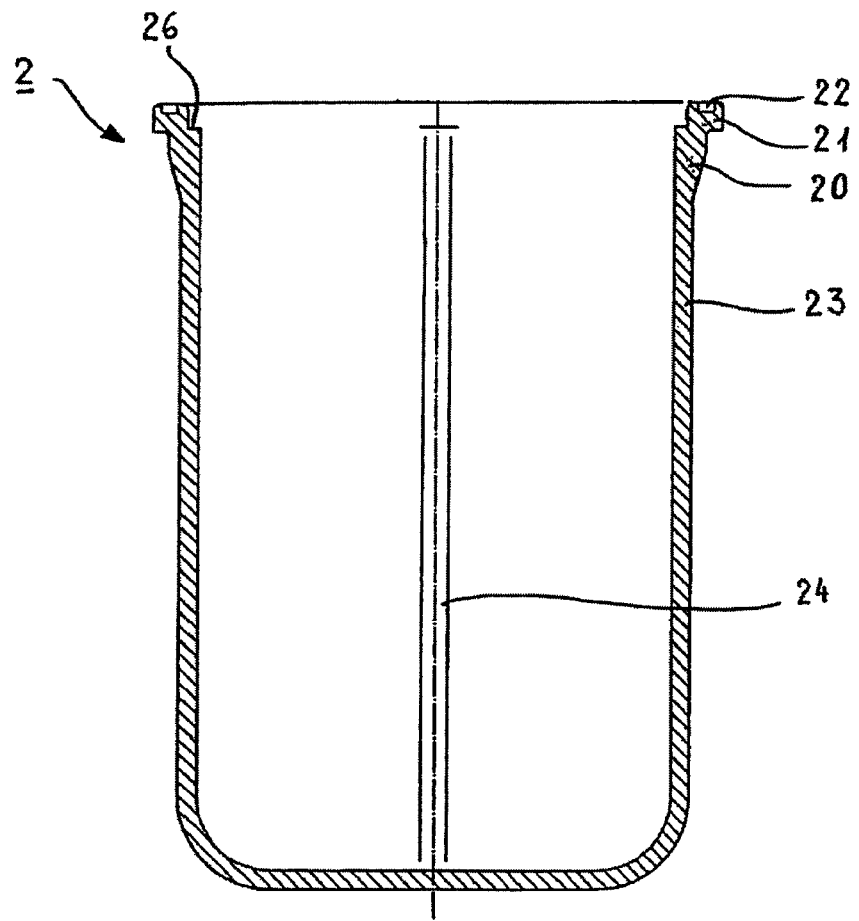
FIG. 4 shows a side view in section of the container body of the container of FIG. 1.

FIG. 1 shows a side view in cross-section of a first embodiment of an evacuatable or pre-evacuated container 1. The container 1 has a substantially cylindrical container body 2 with a bottom 3, and a cover element 4. The cover element 4 is releasably connected to the container body by way of a snap connection 5. As already mentioned, the container body 2 is of a substantially cylindrical configuration. At its end, it has a slightly projecting portion 20 of increasing wall thickness. That also has a portion 21 which further projects. The projecting portion 21 is provided on its side facing away from the container body in the direction of the longitudinal extent thereof, with a peripherally extending groove 22 with inserted seal element 6. The groove 22, as well as the projecting portion 21 and the portion 20 of increased wall thickness, can be better seen in FIG. 4.

Figure 2:
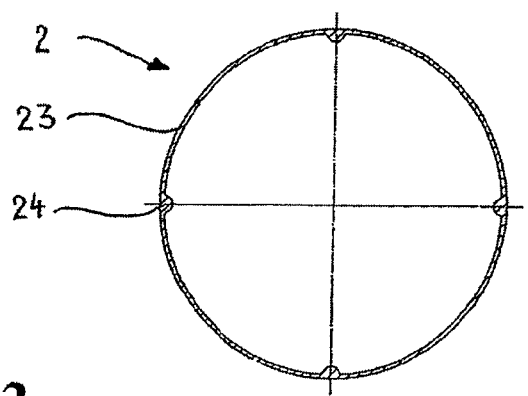
FIG. 2 shows a cross-sectional view through the container of FIG. 1 along line A-A.
Figure 9:
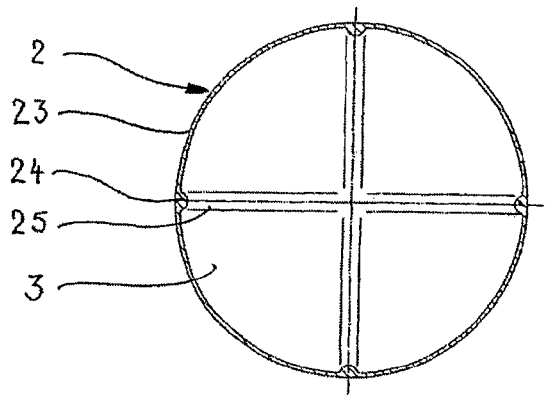
FIG. 9 shows a view in cross-section of a second embodiment of a pre-evacuatable or pre-evacuated container for medical purposes as a plan view on to the bottom of the container body.

On its inward side, that is to say directed towards the interior of the container 1 or the container body 2, the container wall 23 has reinforcing ribs 24. They can be particularly clearly seen from the cross-sectional view of the container body in FIG. 2. The reinforcing ribs 24, of which there are in each case two mutually oppositely disposed reinforcing ribs arranged at an angle of 90° relative to each other in the embodiment of FIG. 1 and FIG. 2, serve to maintain the cylindrical shape of the container body 2, even when the container is evacuated. They therefore serve to stabilize the container body in relation to buckling distortion upon evacuation. In the embodiment of FIG. 2, only the container wall 23 of the container body 2 is provided with the reinforcing ribs in the longitudinal direction. In the embodiment of the container body 2 shown in FIG. 9, the bottom 3 of the container is also provided with reinforcing ribs 25, in which case the reinforcing ribs 24 are extended here in the region of the bottom 3 and cross over each other. That provides that the bottom 3 is still further reinforced.

The cover element 4 of the container 1 may be provided with two connection portions 7, 8 as well as a suspension device 9 on its outside. That can also be seen from FIG. 3. The two connection portions 7, 8 serve for connecting hoses to the container 1, in particular for evacuation thereof, but in particular also for using the container 1 as a Redon flask or for other medical purposes in respect of which it is desirable for liquids etc to be sucked in. The suspension device 9 serves for suspending the container 1, for example, from an infusion stand or another mounting means for holding the container. The minimum and maximum markings on the suspension device can be used for a pressure indication which specifies the minimum and maximum pressures prevailing in the container or the pressure which is therebetween, so that it is possible to establish whether the container can still achieve an adequate suction power for sucking in fluids. Here, for example, a bellows can be fitted on to the connection portions 7 or 8 as the pressure indicator device and appropriately used for indicating the pressure obtaining within the container.

Figure 3:
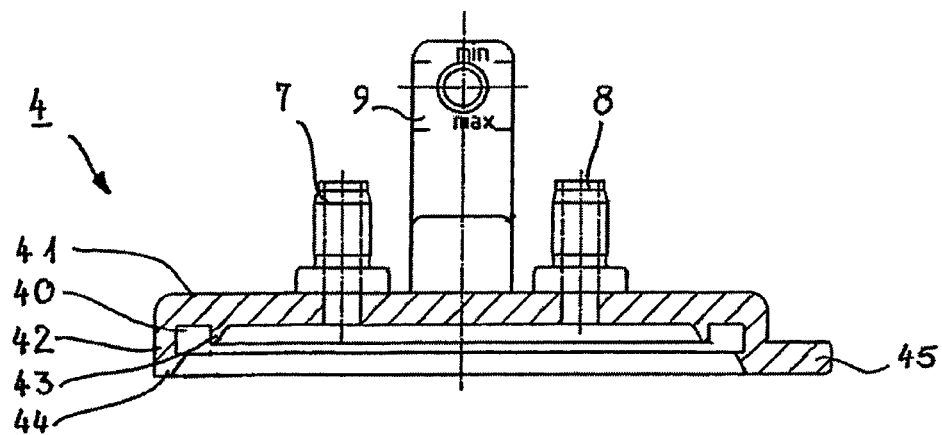
FIG. 3 shows a side view in section of the cover element of the container of FIG. 1.

As can be better seen from FIG. 3, a receiving space 40 may be provided for forming the snap connection 5 and for receiving the projecting portion 21 in the cover element 4. The receiving space 40 is defined by substantially three sides, wherein provided on the one side is a substantially flat portion 41 which forms the actual cover element, provided on the outside of the cover element is an encasing rim portion 42, while provided in the inner region of the cover element 4 is an additional wall portion 43. Furthermore, the rim portion 42 also forms a narrow portion 44 which is directed in a direction towards the container body 2 and which embraces the projecting portion 21 of the container body over a distance, from below. The projecting portion 21 is then disposed within the wall portion 43, a part of the flat portion 41, a part of the rim portion 42 and the portion 44 engaging therebeneath. In addition to the sealing element 6 provided within the groove 22, that affords a stable connection between the cover element 4 and the container body 2 and even further sealing integrity.

In this arrangement, the wall portion 43 is of a configuration such as to narrow in a direction towards the container body, that is to say, in the region of its join to the flat portion 41, it is wider than in its end region. With its straight edge, it bears against the inside of the projecting portion 21 and projects into a step 26 there. That can be particularly clearly seen also from FIG. 1 and FIG. 5. That, therefore, permits it to be securely received in the receiving space 40 of the cover element 4.

Figure 8:
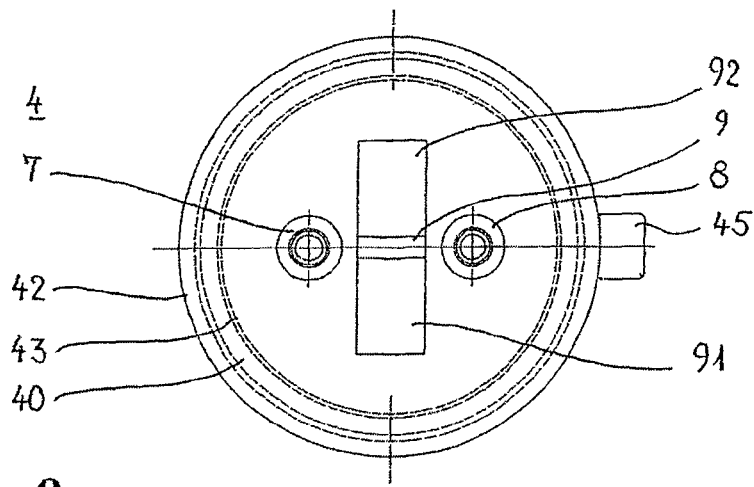
FIG. 8 shows a plan view of the cover element of the container of FIG. 1.

As can further be seen from FIG. 3, the rim portion 42 has a gripping element 45 projecting therefrom at one side. That gripping element 45 can be even better seen from the plan view of the cover element 4 as shown in FIG. 8. The gripping element 45 serves for more easily removing the cover element 4 from the container body 2. Instead of providing only one gripping element 45 as shown in FIG. 8, it is also possible to arrange a plurality of gripping elements 45 distributed over the periphery of the cover element 4. Furthermore, it is possible to provide even a peripherally extending gripping element 45 in projecting relationship from the rim portion 42. It will be noted, however, that in general a small-size gripping element 45, as shown in FIG. 8, is already fully sufficient for better gripping the cover element 4.

Figure 7:
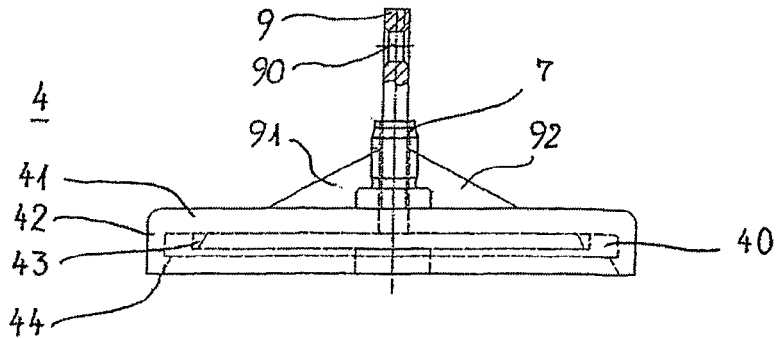
FIG. 7 shows a detail view of the cover element of the container of FIG. 5.

FIG. 7 shows a view of the cover element 4 which is turned through 90° with respect to the view shown in FIG. 3 and in which the suspension device 9 is illustrated in partial section in order here better to show the through opening 90 in the suspension device 9. It will also be seen, like also in the case of the plan view on to the cover element of FIG. 8, that the suspension device 9 is laterally supported by way of inclinedly extending support struts 91, 92 in order to impart better stability to the suspension device 9. Those support struts 91, 92, however, can also be omitted, like also the suspension device 9 itself in its entirety, if the support struts 91, 92, or the suspension device 9 should not be required for the respective purpose of use.

Figure 5:
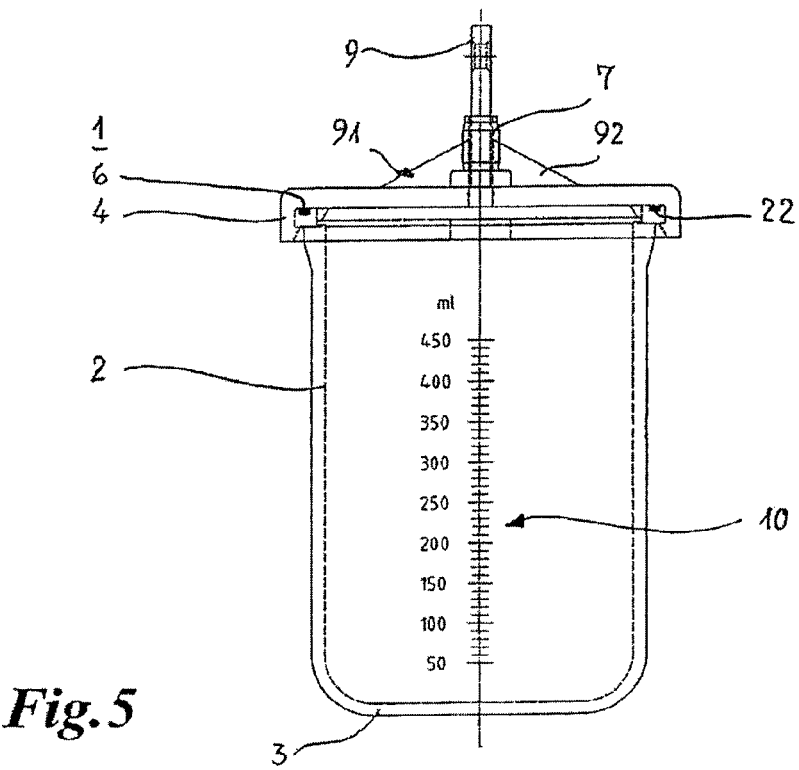
FIG. 5 shows a side view of the container of FIG. 1 turned through 90° with scale means fitted thereto.
Figure 6:
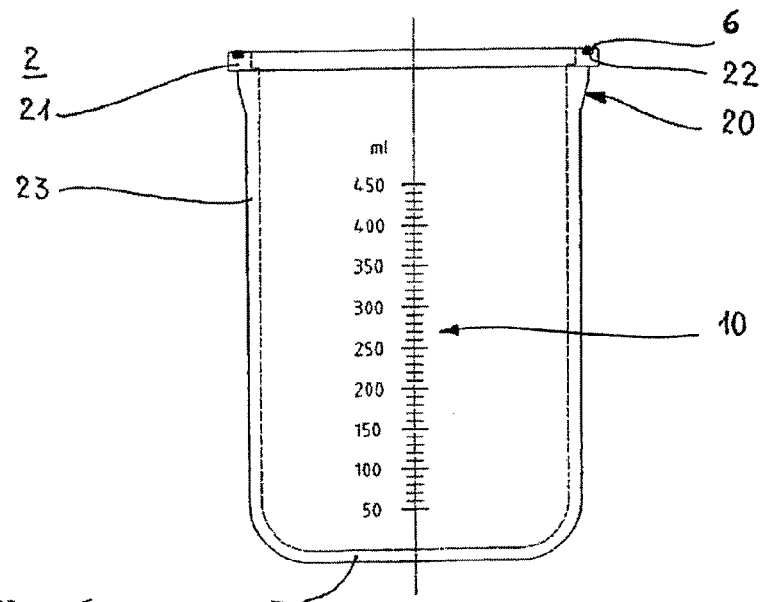
FIG. 6 shows a side view of the container body with scale means shown in FIG. 5.

FIG. 5 shows the container 1 of FIG. 1 in a position of being turned through 90° and provided with a scale means 10. FIG. 6 only shows the container body 2, also provided with the scale means 10. The sealing element 6 in this case is already fitted into the groove 22, in which respect the sealing element 6 may comprise an O-ring seal. The cover element 4 only has to be fitted on to the container body 2, as shown in FIG. 7, in order to arrive at the assembled condition as shown in FIG. 5. The scale means 10 serves to be able to read off the filling amount in the container during use as a suction removal device for sucking away for example body fluids.

In certain embodiments, the provision of the reinforcing ribs 24, 25 allows for the wall thickness of the container wall 23 to be selected to be only in the region of 1 mm. It will be appreciated that smaller wall thicknesses can also be adopted, for example, when there are more than four reinforcing ribs, or it is also possible to adopt larger wall thicknesses. In regard to the dimensioning of the peripherally extending groove 22, it may comprise a depth of 1 to 2 mm and a width of about 2 to 3 mm. It will be appreciated that other dimensions are also possible here, in which respect the choice of the dimensions of the groove 22 and the sealing element 6 are optimized relative to each other to permit optimum sealing integrity.

Besides the embodiments of pre-evacuated or pre-evacuatable containers for medical purposes, which are described hereinbefore and illustrated in the drawings, numerous other embodiments can also be designed, in which the respective container wall of the container body is provided at its end with a groove into which a sealing element is fitted in order to permit a sealing action in relation to a cover element of the container.

Although the foregoing description has shown, described, and pointed out the fundamental novel features of the present teachings, it will be understood that various omissions, substitutions, and changes in the form of the detail of the apparatus as illustrated, as well as the uses thereof, may be made by those skilled in the art, without departing from the scope of the present teachings. Consequently, the scope of the present teachings should not be limited to the foregoing discussion, but should be defined by the appended claims.

What is claimed is:

1. A pre-evacuatable or pre-evacuated container for medical purposes, comprising a container body, a cover and a sealing element for sealingly engaging the container body to the cover when the cover is locked on the container body, wherein:

the container body comprises a bottom, a wall extending upward from said bottom defining a cavity, and an open end, the wall comprising a side wall portion and a projecting portion disposed near the open end of the container body, the projecting portion comprising a first upward-facing flat surface perpendicular to said wall, a second upward-facing surface perpendicular to said wall and forming an inward-facing step, and an outward-facing protrusion having a downward-facing surface, the first upward-facing flat surface comprising a groove within said upward-facing flat surface into which the sealing element is inserted, said groove being dimensioned such that said sealing element is fully disposed within said groove when the cover is locked on the container body, a wall thickness below the inward-facing step greater than a thickness of the side wall;

the cover comprises a receiving space for receiving the projecting portion therein, said receiving space having a flat surface for contacting said sealing element and said flat surface facing downward;

a gripping element disposed on a perimeter of the cover;

the cover and the container body are configured to sealingly engage one another so as to encompass the cavity within said container and to sealingly engage said respective flat surfaces by compressing said sealing element within said groove when the cover is locked on the container body;

so that during medical use, said container is capable of sucking in and containing fluids within said cavity when evacuated;

said container is capable of maintaining a reduced pressure within said cavity in the absence of an applied vacuum; and the container is evacuatable to a reduced pressure of at least 90,000 Pascals below atmospheric pressure.

2. The container according to claim 1, wherein the sealing element is in the form of an O-ring seal.

3. The container according to claim 1, wherein the projecting portion is adjacent the open end of the container and has a greater wall thickness than the wall thickness of other portions of said wall.

4. The container according to claim 1, wherein the sealing element is releasably connected to the container body.

5. The container according to claim 4, further comprising a clamping or snap connection for maintaining an engagement of the cover to the container body.

6. The container according to claim 1, wherein the cover and the container body are fixedly connectable or connected together.

7. The container according to claim 1, wherein at least one of the container body and the cover comprise a plastic material.

8. The container of claim 7, wherein the plastic material comprises one of polyvinyl chloride (PVC), polypropylene (PP), or polyethylene terephthalate (PETP).

9. The container according to claim 1, wherein the container body additionally comprises at least one reinforcing rib.

10. The container according to claim 9, further comprising respectively mutually oppositely disposed said reinforcing ribs.

11. The container of claim 10, further comprising four of said reinforcing ribs.

12. The container according to claim 9, wherein the at least one said reinforcing rib extends along the container wall.

13. The container according to claim 9, wherein the at least one said reinforcing rib extends along said wall and said bottom.

14. The container according to claim 1, further comprising a scale.

15. The container according to claim 1, wherein the cover comprises at least one connection portion for the connection of a hose.

16. The container according to claim 1, wherein the cover comprises at least one suspension device for suspending the container from a holding device.

17. The container according to claim 16, wherein the holding device comprises an infusion stand.

18. The container according to claim 1, wherein the cover further comprises a rim portion which adjoins the downward-facing flat surface and which is angled substantially at a right angle relative thereto, and an inward flange which is so arranged at a spacing relative to the rim portion such that the receiving space is between the rim portion and the flange.

19. The container according to claim 18, wherein said flange sealingly engages said downward-facing surface of the projecting portion of the container body.

20. The container according to claim 1, wherein the wall portion narrows in a direction distal-to-proximal to the bottom.

21. The container according to claim 1, wherein the downward facing surface of said protrusion has a dimension for engaging an upward-facing rim portion of said cover and locking said cover to said container by a snap-fit.

22. A pre-evacuatable or pre-evacuated container for medical purposes, comprising a container body, a cover and a sealing element for sealingly engaging the container body to the cover when the cover is locked on the container body, wherein:

the container body comprises a bottom, a wall extending upward from said bottom defining a cavity, and an open end, the wall comprising a side wall portion and a projecting portion disposed near the open end of the container body, the projecting portion comprising a first upward-facing flat surface perpendicular to said wall, a second upward-facing surface perpendicular to said wall and forming an inward-facing step, and an outward-facing protrusion having a downward-facing surface, the first upward-facing flat surface comprising a groove within said upward-facing flat surface into which the sealing element is inserted, said groove being dimensioned such that said sealing element is fully disposed within said groove when the cover is locked on the container body, a wall thickness below the inward-facing step greater than a thickness of the side wall;

the cover comprises a receiving space for receiving the projecting portion therein, said receiving space having a flat surface for contacting said sealing element and said flat surface facing downward;

so that during medical use, said container is capable of sucking in and containing fluids within said cavity when evacuated;

said container is capable of maintaining a reduced pressure within said cavity in the absence of an applied vacuum; and the container is evacuatable to a reduced pressure of at least 90,000 Pascals below atmospheric pressure wherein the cover and the container body are welded together.

\* \* \* \* \*